(12) United States Patent
Wagner

(10) Patent No.: US 10,840,652 B2
(45) Date of Patent: Nov. 17, 2020

(54) CONNECTED COMPONENT AUTHENTICATION

(71) Applicant: ACIST Medical Systems, Inc., Eden Prairie, MN (US)

(72) Inventor: Reed B. Wagner, Bloomington, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 191 days.

(21) Appl. No.: 15/968,059

(22) Filed: May 1, 2018

(65) Prior Publication Data

US 2018/0323553 A1 Nov. 8, 2018

Related U.S. Application Data

(60) Provisional application No. 62/500,099, filed on May 2, 2017.

(51) Int. Cl.
*H01R 13/68* (2011.01)
*G01R 27/02* (2006.01)
(Continued)

(52) U.S. Cl.
CPC .............. *H01R 13/68* (2013.01); *A61B 90/90* (2016.02); *A61M 5/5086* (2013.01); *A61M 39/10* (2013.01); *G01R 27/02* (2013.01); *G05B 15/02* (2013.01); *G05G 1/02* (2013.01); *G06F 21/44* (2013.01); *G06F 21/70* (2013.01); *A61B 90/37* (2016.02); *A61B 2090/0805* (2016.02); *A61B 2090/0814* (2016.02); *A61B 2090/374* (2016.02); *A61B 2090/3735* (2016.02); *A61B 2090/3762* (2016.02); *A61B 2090/3782* (2016.02); *A61M 5/14* (2013.01);
(Continued)

(58) Field of Classification Search
CPC ............ G07C 9/00103; G07C 9/00111; G07C 9/00309; G07C 9/00571; G07C 9/00126; G07C 9/00158; G07C 9/00166; G07C 9/00007; G07C 2209/63; G07C 9/00; G07C 9/00031
USPC ......................................................... 340/5.2
See application file for complete search history.

(56) References Cited

U.S. PATENT DOCUMENTS 9,070,683 B2 * 6/2015 Fender .................... H01L 22/34
2014/0114610 A1 * 4/2014 Sako ........................ G07C 3/00
702/182

(Continued)

OTHER PUBLICATIONS

Brooks et al., "Fusing Currents in Traces," 2015, 18 pages.

*Primary Examiner* — James J Yang
(74) *Attorney, Agent, or Firm* — Fredrikson & Byron, P.A.

(57) ABSTRACT

Methods, devices, and systems for authenticating a component are disclosed herein. One such component can be a control device. This control device can include a first button and a control device fitting. When activated, the first button can be configured to cause a first control signal to be output from the control device to a controllable component. The control device fitting can include a connection device having a connector element and a conductive authentication element. The connector element can be configured to connect the control device to the controllable component. The conductive authentication element can be configured to allow the controllable component to authenticate the control device for use with the controllable component.

20 Claims, 4 Drawing Sheets

(51) Int. Cl.
*G05B 15/02* (2006.01)
*G06F 21/70* (2013.01)
*A61M 39/10* (2006.01)
*A61M 5/50* (2006.01)
*G05G 1/02* (2006.01)
*G06F 21/44* (2013.01)
*A61B 90/90* (2016.01)
*A61B 90/00* (2016.01)
*A61M 5/14* (2006.01)

(52) U.S. Cl.
CPC .............. *A61M 2039/1022* (2013.01); *A61M 2205/6018* (2013.01); *A61M 2205/6027* (2013.01); *G06F 2221/2129* (2013.01); *H01R 2201/12* (2013.01)

(56) References Cited

U.S. PATENT DOCUMENTS

2019/0005216 A1* 1/2019 Yakishyn ................ G06F 21/32
2019/0213810 A1* 7/2019 Lundberg ................ H04L 9/088

* cited by examiner

CONNECTED COMPONENT AUTHENTICATION

RELATED APPLICATION

This application claims the benefit of U.S. Provisional Application No. 62/500,099 filed May 2, 2017, the contents of which are hereby incorporated by reference.

TECHNICAL FIELD

This disclosure generally relates to devices, systems, and methods for authenticating a component, such as for authenticating a first component that is connectable to a second component.

BACKGROUND

Across a number of industries, reuse of one or more component parts in a system can be undesirable. However, system operators may be tempted to reuse such components more than a suitable number of times, for instance in an attempt to reduce costs. For example, in the medical device field many systems are operated in applications that require a sterile environment. In some cases, reuse of certain components in a system more than a predetermined number of times may be inconsistent with preserving the sterile environment. In other cases, whether in the medical device field or other industries, reuse of certain components in a system more than a predetermined number of times may raise quality control concerns.

SUMMARY

Various exemplary embodiments are described herein for authenticating a component. In one example, this disclosure describes devices, systems, and methods useful in determining if a first component that is connectable to a second component is authentic. Whether a connected component is determined to be authentic can vary depending on the application. In one example, a connected component may not be authentic if the connected component has been used previously a predetermined number of times (e.g., once). Where a determination has been made that the connected component has been used previously the predetermined number of times, some such embodiments may be able to prevent the connected component from being used. Where a determination has been made that the connected component has not been used previously the predetermined number of times, some such embodiments may be able to reconfigure the connected component so that it cannot be used upon a subsequent connection. In this way, embodiments disclosed herein can be useful in some applications in authenticating a connectable component and thereby helping to preserve a sterile environment and/or reduce quality control concerns.

Features disclosed herein can be useful across a wide variety of applications. The particular type of connectable component can vary depending on the specific application. An example of a connectable component described herein for illustrative purposes is a control device. Such a control device can be connectable to a controllable component in order to convey a control signal to the controllable component when connected thereto.

One exemplary embodiment includes a control device. In this embodiment, the control device includes a first button and a control device fitting. When activated, the first button can be configured to cause a first control signal to be output from the control device to a controllable component. The control device fitting can be at the control device. The control device fitting can include a connection device having a connector element and a conductive authentication element. The connector element can be configured to connect the control device to the controllable component. The conductive authentication element can be configured to allow the controllable component to authenticate the control device for use with the controllable component.

In a further exemplary embodiment of this control device, the conductive authentication element can include a first contact trace and a sensing trace that is spaced from the first contact trace. The first contact trace can be configured at the connection device so as to contact a first electrical output at the controllable component when the connector element is connected to the controllable component. The sensing trace can have an associated authentication value usable by the controllable component to authenticate the control device. In one example, the authentication value associated with the sensing trace usable by the controllable component to authenticate the control device can be an impedance value of the sensing trace. In another example, the authentication value associated with the sensing trace usable by the controllable component to authenticate the control device can be a time is takes to fuse the sensing trace.

Another exemplary embodiment includes a system for authenticating a control device. In this embodiment, the system includes a controllable component and a control device. The controllable component can store a predetermined value. The control device can be in communication with the controllable component. The control device can include a first button and a control device fitting. When activated, the first button can be configured to output a first control signal to the controllable component. The control device fitting can include a connection device having a connector element and a conductive authentication element. The connector element can be configured to connect the control device to the controllable component. The conductive authentication element can include an associated authentication value. The controllable component can be configured to measure the authentication value associated with the conductive authentication element and compare this measured authentication value to the predetermined value. When the measured authentication value matches the predetermined value, the controllable component can determine that the control device is authentic.

In a further exemplary embodiment of this system, the conductive authentication element includes a sensing trace that defines the authentication value. In this further embodiment, the predetermined value may be selected from a group consisting of i) a range of impedance values of the sensing trace, and ii) a range of times it takes for the controllable component to fuse the sensing trace. In some cases, after the controllable component has determined that the control device is authentic, the controllable component can be configured to change the authentication value defined by the sensing trace to differ from the predetermined value. For instance, the controllable component can be configured to change the authentication value by fusing the sensing trace when the control device is connected to the controllable component. Also in some cases, when the controllable component determines that the control device is authentic the controllable component can use the first control signal. But, when the measured authentication value does not match the predetermined value the controllable component can determine that the control device is not authentic and the controllable component may not use the first control signal.

An additional exemplary embodiment includes a method for authenticating a first component. In this embodiment, the method includes connecting the first component to a second component, outputting a current from the second component onto a conductive authentication element of the first component, and measuring an authentication value associated with the conductive authentication element. The method may further include comparing the measured authentication value to a predetermined value and, when the measured authentication value matches the predetermined value, determining that the first component is authentic. In some cases, when the first component is determined to be authentic, the second component uses a control signal received from the first component. Also, in some cases, after determining that the first component is authentic, the method can include changing the authentication value to differ from the predetermined value by fusing the conductive authentication element.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

DETAILED DESCRIPTION

The following detailed description is exemplary in nature and provides some practical illustrations and examples. Those skilled in the art will recognize that many of the noted examples have a variety of suitable alternatives.

Figure 1:
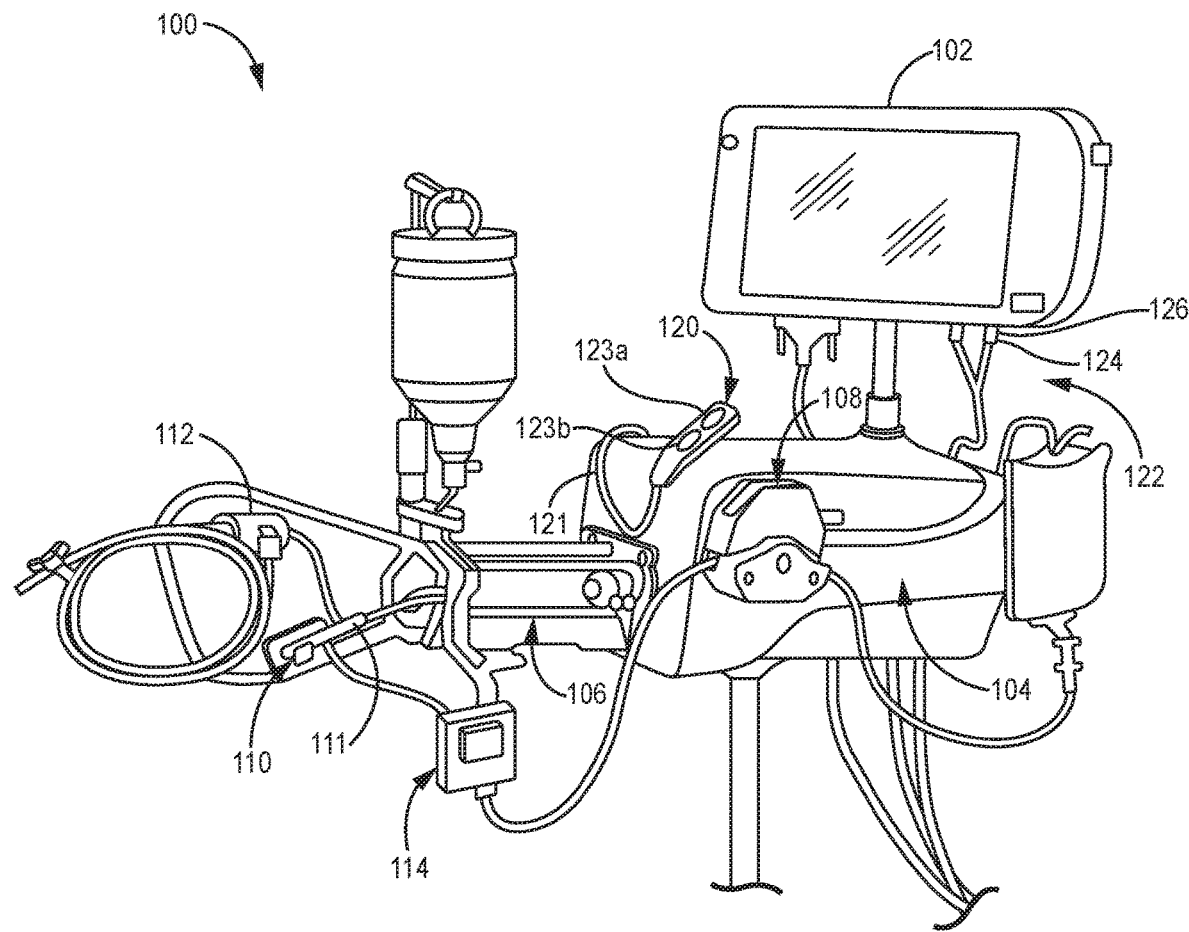
FIG. 1 is a perspective view of an exemplary embodiment of an injection system.

FIG. 1 illustrates a perspective view of an exemplary embodiment of an injection system 100. The injection system 100 can operate to inject a quantity of fluid into a vessel of a patient, for instance via a catheter assembly at the patient. The fluid injected by the system 100 can be, for example, a contrast fluid, a non-contrast fluid (e.g., saline), or a combination thereof. A variety of medical diagnostic and/or interventional procedures can be performed in connection with the system 100. These procedures can include, for instance, optical coherence tomography (OCT) imaging, intravascular ultrasound (IVUS) imaging, computed tomography (CT) imaging, magnetic resonance (MRI) imaging, angiographic procedures, and interventional device procedures.

The system 100 as illustrated in FIG. 1 includes a control panel 102. The control panel 102 can serve as the operational interface for the system 100. As such, the control panel 102 can include one or more processors, or be in communication with one or more remote processors, as well as local memory storing non-transitory computer executable instructions run by the one or more processors in response to operator input. An operator of system 100 can use control panel 102 to set up various parameters and/or protocols to be used for a given injection procedure. In one example, the operator can interact with control panel 102 to input injection parameters such as flow rate, injection volume (e.g., maximum), injection pressure (e.g., maximum), rise time, and/or other injection parameters. In one embodiment, control panel 102 includes a touch-screen panel display, enabling an operator to view and modify injection parameters as desired. Control panel 102 can also be used to initialize system 100 (e.g., to prepare it for a patient injection) and/or to activate certain features or sequences of system 100 operation.

The control panel 102 can be in communication with component devices of system 100. The control panel 102, as the operational interface, can receive data from and/or send control signals to such component devices of the system 100. These devices can include, for instance, one or more of injector head 104 (including a powered injector motor drive for advancing or retracting a plunger fit within a syringe 106), pump 108 (e.g., a peristaltic pump), patient manifold sensor 110 (e.g., to sense a position of a fluid valving system 111), air detector 112, and/or pressure transducer 114.

In some cases, it may be useful to control the system 100 remote from the control panel 102. Accordingly, the illustrated system 100 further includes a control device 120 which may be designed to be held in a hand of a user of the system 100 and thus, in such cases, could be referred to as a hand control device. The control device 120 can be in communication with the control panel 102 and thereby send control signals for the system 100 to the control panel 102. In other embodiments the control device 120 can be in communication with one or more remote processors of the system 100 and route control signals through the control panel 102. In the illustrated embodiment, the control device 120 is in communication with the control panel 102 via a communication line 121 though in other examples the control device 120 could be connected to the control panel 102 without the communication line 121. The control device 120 can allow an operator to control some or all functions of the system 100 remote from the control panel 102 as convenient in various applications of the system 100. As such, the control device 120 may be referred to as an example of a control device and the system 100 can the control panel 102 (e.g., and/or other components of the system 100 in communication with the control panel 102) may be referred to as an example of a controllable component.

The control device 120 can include one or more user-activated elements for conveying one or more control signals related to operation of the system 100. In the embodiment shown here, the control device 120 includes a button 123a and a button 123b. Activating the button 123a or the button 123b can cause the control device 120 to send a corresponding control signal to the control panel 102 or other component of the system 100. The corresponding control signals from the buttons 123a and 123b can relate to different fluid types capable of being delivered by the system 100, for example a first fluid type such as contrast fluid and a second fluid type such as saline.

For instance, when the button 123a is activated the button 123a can be configured to cause a first control signal to be output from the control device 120 via the communication line 121. This first control signal may correspond to, for instance, a first fluid type fluid delivery rate command for the controllable component. The first control signal can be processed at the control panel 102 to cause the appropriate components of the system 100 to start or stop delivery of the first fluid type and/or vary the rate at which the first fluid type is being delivered from the system 100. In one example, this button 123a can be pressure-sensitive in its activation such that as the user applies varying pressure to the button 123a the corresponding first fluid type fluid delivery rate command output from the control device 120 will vary accordingly. Thus, the button 123a may allow the user to control the rate at which the system 100 delivers a first fluid type to a patient in an instantaneous, convenient manner in addition to allowing the user to initiate or terminate delivery of the first fluid type (e.g., when the button 123a is first activated, when the button 123a is no longer activated).

When the button 123b is activated the button 123b can be configured to cause a second control signal to be output from the control device 120 via the communication line 121. This second control single may correspond to, for instance, a second fluid type start/stop fluid delivery command for the controllable component which can be processed at the control panel 102 to cause appropriate components of the system 100 to start or stop delivery of the second fluid type from the system 100. Various other user-activated elements can also be included at the control device 120 as suited for a particular application. The control device 120 can be configured to convey the one or more control signals in the form of an electrical signal, pneumatic pressure signal, or other form suitable for conveying particular commands.

To facilitate communication with the system 100, the control device 120 is removably coupled to the control panel 102, or other device of the system 100, via a connection 122. The connection 122 includes a control device fitting 124 and a control panel fitting 126. The control device fitting 124 may, in some cases, be located at the communication line 121, such as at an end portion of the communication line 121 opposite an end portion of the communication line 121 at the control device 120. In some embodiments, the control device 120 can be considered to include the communication line 121 and control device fitting 124 though in other cases the control device fitting 124 can be configured to connect the control device 120 to the control panel 102, or other system 100 component, without the communication line 121. The control panel fitting 126 may be located at a surface of the control panel 102 and it can include one or more contacts, such as one or more pins (e.g., spring loaded pogo pins), capable of outputting an electric current. Though, in other embodiments, these one or more contacts can be located on another component of the system 100. As one example, the connection 122 can be a Luer connection between the fittings 124 and 126 (e.g., where the control device fitting 124 is one of a male Luer connector and a female Luer connector and the control panel fitting 126 is the other of a male Luer connector and a female Luer connector including one or more contacts). In some cases, such as in the embodiment illustrated in FIG. 1, the connection 122 can further include a second control device fitting and a corresponding second control panel fitting. In such cases, the second control device fitting and the corresponding second control panel fitting may be the same or similar to the fittings 124 and 126 as described herein. For instance, the second control device fitting can be one of a male or female Luer connector while the control device fitting 124 is the other of a male or female Luer connector.

In many applications of the system 100, it can be desirable to replace the control device 120 (e.g., including the communication line 121 and control device fitting 124) with a new control device to preserve a sterile environment and/or help reduce potential quality control issues from arising. Indeed, in some instances this can be desirable after a single use. To do so, the connection 122 can be uncoupled, such as by removing the control device fitting 124 from the control panel fitting 126, and a control device fitting of a new control device can then be similarly coupled to the control panel 102 at the control panel fitting 126.

In many cases, when connected, it may be useful to authenticate the new, replacement control device 120. Authenticating the connected control device 120 may ensure that the particular connected control device is appropriate for use with the system 100. As an example, authenticating the connected control device 120 can include determining if the connected control device 120 has been used previously a predetermined number of times. In one instance, an authentic control device is a control device that has not been used any previous time. In certain cases, authenticating the connected control device 120 may be useful in maintaining a sterile environment and/or reducing potential quality control issues. Although the control device 120 is used as an example in this disclosure, any replaceable, connectable component of the system 100, or any other system, can incorporate features described herein for authentication.

Figure 2:
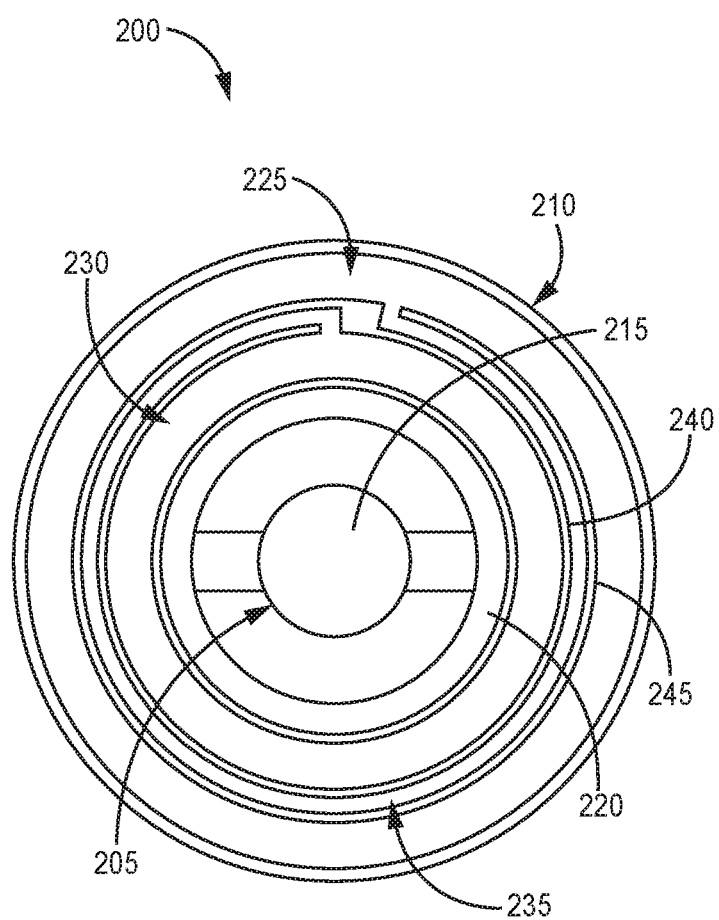
FIG. 2 is a schematic diagram of an exemplary embodiment of a connection device useful for authenticating a connected component.

FIG. 2 illustrates a schematic diagram of an exemplary embodiment of a connection device 200 useful for authenticating a connectable component. FIG. 2 shows a bottom plan view of the control device fitting, described previously, having the connection device 200. The example of the control device connectable to the control panel and injection system as the controllable component will be referenced, but the disclosed features can be implemented in a variety of other connectable control devices and controllable components.

The illustrated exemplary connection device 200 includes a connector element 205 and a conductive authentication element 210. In the embodiment disclosed here, the connector element 205 is a Luer connector, though in other embodiments the connector element 205 can take a number of other suitable connection structures, including a threaded connector, a movably biased interference connector, and/or an adhesion connector. The connector element 205 (e.g., a male Luer connector) can be used for removably coupling the control device to the control panel. The conductive authentication element 210 can be adjacent the connector element 205. The conductive authentication element 210 can include, as examples, a printed circuit board, a deposited layer of conductive ink, a deposited layer of indium tin oxide or one or more other suitable conductive mediums. The conductive authentication element 210 can be configured to allow the controllable component, such as the control panel and injection system, to authenticate the control device for use with the controllable component. Thus, the conductive authentication element 210 may be used, at least in part, to provide authentication capability upon connection of the control device to the control panel. In the illustrated embodiment, the conductive authentication element 210 can be a one-sided single layer printed circuit board having one or more traces but in another embodiment such printed circuit board could be a multi-layer board having one or more traces.

In the case of the connector element 205 in the form of a Luer connector, the connector element 205 can include a central extension 215 that is adapted to be received within a female Luer connector, for instance, of the control panel fitting. The Luer connector, as shown here, can also include a perimeter ring 220 adapted to secure the conductive authentication element 210 to connector element 205. As shown in the exemplary embodiment here, the perimeter ring 220 can bound the central extension 215 and thus be disposed between the central extension 215 and the conductive authentication element 210. For example, the perimeter ring 220 can have upper and lower surfaces defining an intermediate slot therebetween. The perimeter ring 220 can thus be configured to provide a fit, such as an interference fit, at the intermediate slot for receiving the conductive authentication element 210 (e.g., via a "snap fit"). In another embodiment, the conductive authentication element 210 can be deposited directly at the connector element 205.

The conductive authentication element 210 can include a number of traces. In the example shown here, the conductive authentication element 210 includes a first contact trace 225, a second contact trace, 230, and a sensing trace 235. The first contact trace 225 can be configured at the connection device 200 so as to contact a first electrical output, such as a first pin, at the control panel fitting and the second contact trace 230 can be configured at the connection device 200 so as to contact a second electrical output, such as a second pin, at the control panel fitting when the connector element 205 is connected to the control panel fitting (e.g., when the central extension 215 is received within the female Luer connector at the control panel fitting). Accordingly, the first and second contact traces 225 and 230 can be spaced apart a distance that corresponds to the spacing between the first and second pins at the control panel fitting. As shown here, each of the first contact trace 225 and the second contact trace 230 can have an area that is greater than an area of the sensing trace 235.

The sensing trace 235, as illustrated here, is located between the first contact trace 225 and the second contact trace 230. An inner wall 240 can separate the second contact trace 230 from the sensing trace 235 and an outer wall 245 can separate the first contact trace 225 from the sensing trace 235. As examples, the inner wall 240 and outer wall 245 can be made of an insulating material. Each of the inner wall 240 and outer wall 245, as shown, can include a gap in some cases. The gap could be a void in the substrate material of the conductive authentication element 210 and may impact the fusing time of the conductive authentication element 210, as described further below. The conductive authentication element 210 can be enclosed by a suitable insulating member. For instance, in the illustrated embodiment, the conductive authentication element 210 can be enclosed by a gasket at the second fitting interfacing with the perimeter of the conductive authentication element 210, a backing material (e.g., composed of an insulating material) at a back side (not shown) of the conductive authentication element 210, and the second fitting at the front side of the conductive authentication element 210.

Connecting the control connection device 200 to the controllable component, such as the control panel and/or injection system, can allow the controllable component to determine if the control device is an authentic component. For instance, computer executable instructions can be stored at the control panel, or other system component, and run by the one or more processors at the control panel, or other system component, to perform one or more connected component authentication techniques. The sensing trace 235 can have an authentication value usable by the controllable component, such as the control panel and/or injection system, to authenticate the control device. As such, the control panel can be preprogrammed with a predetermined value (e.g., a predetermined range) for the sensing trace 235. The control panel can then measure the corresponding authentication value of the sensing trace 235 when the connection device 200 is connected to the control panel. Depending on whether the authentication value of the sensing trace 235 falls within the predetermined value preprogrammed at the control panel, the control panel can determine if the control device is authentic. In another example, such computer executable instructions can be stored at a different component of the system and/or run by one or more processors at a different component of the system to perform one or more connected component authentication techniques.

As one particular example, the control panel can measure an impedance value of the sensing trace 235 as the authentication value to determine if the control device is authentic. The control panel can be preprogrammed with a predetermined range for the impedance value of sensing trace 235. When the control device is connected to the control panel, the control panel can measure the impedance value of the sensing trace 235. Depending on whether this measured impedance value falls within the predetermined value range preprogrammed at the control panel, the control panel can determine if the control device is authentic.

As another particular example, the control panel can measure the time it takes to fuse the sensing trace 235 at a set current level (e.g., output from the one or more pins at the control panel fitting) as the authentication value to determine if the control device is authentic. The control panel can be preprogrammed with a predetermined range for the fuse time value of the sensing trace 235. For instance, expected fusing time can be estimated according to the formula $t=0.0346(A/I)^2$ where t is in seconds, I is the set current level from the control panel in amps, and A is the cross-sectional area of the one or more traces (e.g., sensing trace 235) is square millimeters. As an example, where the sensing trace 235 has a width of 4 millimeters and a thickness of 0.685 millimeters and the current level from the control panel is set at 1 amp, fusing temperature would be estimated to be reached in approximately 0.26 seconds. In this example, the predetermined value range preprogrammed at the control panel can be centered at 0.26 seconds and bounded on each end of the range according to a margin of error (e.g., ±5%, 10%, 15%, 20%, 25%, etc.). Such margin of error could be set to account for error in the estimated expected fusing time due to thermal properties of materials surrounding the one or more traces. When the control device is connected to the control panel, the control panel can measure the time it takes to fuse the one or more traces (e.g., sensing trace 235). Depending on whether the measured fusing time value falls within the predetermined value range preprogrammed at the control panel, the control panel can determine if the control device is authentic.

In a further example, the control panel can determine if the control device is an authentic component by using both impedance value and time to fuse as the authentication value of the sensing trace 235. In this example, the control panel can first determine if the measured impedance value falls within the predetermined impedance value range preprogrammed at the control panel. If it does, then the control panel can determine if the measured fusing time value falls within the predetermined fusing value range preprogrammed at the control panel.

Accordingly, in this example, if both the impedance value and the time to fuse fall within the respective preprogrammed ranges the control panel can authenticate the control device.

Using any authentication technique, if it is determined that the control device is not authentic the control panel may prevent the control device from being used with the system. For instance, if the control panel determines that the control device is not authentic the control panel may not use control signals from the control device. If so determined, the control panel may display a message indicating that the control device is not authentic and that the control device will not work to operate the system. In some cases, if the control panel has determined that the control device is not authentic, the control panel may prevent the system from operating while this control device is connected.

On the other hand, using any authentication technique, if it is determined that the control device is authentic, the control panel can allow the connected control device to be used with the system.

In addition, in certain embodiments, if the control panel determines that the connected control device is authentic the control panel can be adapted to reconfigure the connection device 200. The control panel can reconfigure the connection device 200 in any manner that will allow the control panel, upon a subsequent connection of the control device, to ascertain whether the control device has been previously used a predetermined number of times. For instance, where an authentic control device is one that has not been used previously, the control panel can be adapted to reconfigure the connection device 200 upon a first connection in a way that will prevent the control panel from determining that the control device is authentic upon a second connection. Similarly, where an authentic control device is one that has been used multiple predetermined times, the control panel can be adapted to reconfigure the connection device 200 incrementally in a manner corresponding to a number of previous connections. For instance, the control panel can be adapted to reconfigure the authentication value associated with the conductive authentication element (e.g., of the sensing trace 235) by changing authentication value associated with the conductive authentication element. This can thereby allow the control panel to determine that the control device is not authentic upon the predetermined number of connections.

In one such embodiment, the control panel can be adapted to reconfigure the connection device 200 of an authentic control device by fusing one or more traces of the connection device 200, such as the sensing trace 235 to reconfigure the authentication value of the sensing trace 235. As one example, once the control panel has determined that the control device is authentic, the control panel can be adapted to output potential (e.g., from one or more pins at the control panel fitting) onto the connection device 200 in order to fuse the sensing trace 235. Fusing the sensing trace 235 can change the authentication value of the sensing trace 235 such that a measured value (e.g., impedance value and/or time to fuse) of the sensing trace 235 will fall outside of a predetermined range for such value upon a subsequent connection of the control device. Accordingly, upon this subsequent connection of the control device, the control panel can determine that the control device is not authentic, because the authentication value of the sensing trace 235 now falls outside of the predetermined range for this value, and may prevent the control device from being used with the system.

Figure 3:
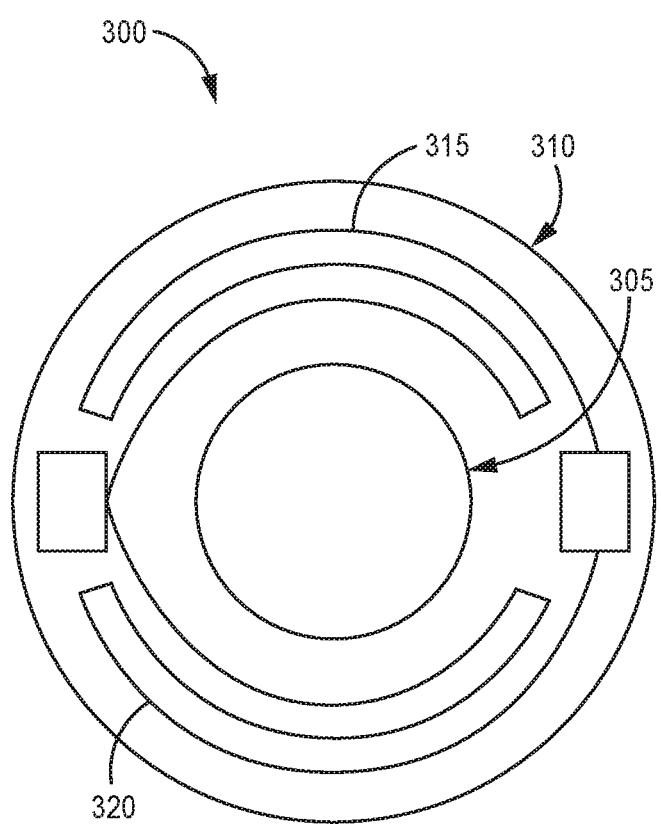
FIG. 3 is a schematic diagram of another exemplary embodiment of a connection device useful for authenticating a connected component.

FIG. 3 illustrates a schematic diagram of another exemplary embodiment of a connection device 300 useful for authenticating a connected component. FIG. 3 shows a bottom plan view of the control device fitting, described previously, with the connection device 300. The connection device 300 is similar to that described above in conjunction with the connection device shown in FIG. 2. Namely, the connection device 300 includes a Luer connector 305 and a conductive authentication element 310. However, the conductive authentication element 310 of the connection device 300 is different in that two sensing traces 315 and 320 are included. The sensing traces 315 and 320 are arranged in parallel. When the connection device 300 is brought into contact with pins at the control panel fitting (e.g., at the two opposite contact pads on the conductive authentication element 310 where the control panel fitting includes two pins), the impedance value can be measured and/or the sensing traces 315 and 320 can be fused as explained herein.

Figure 4:
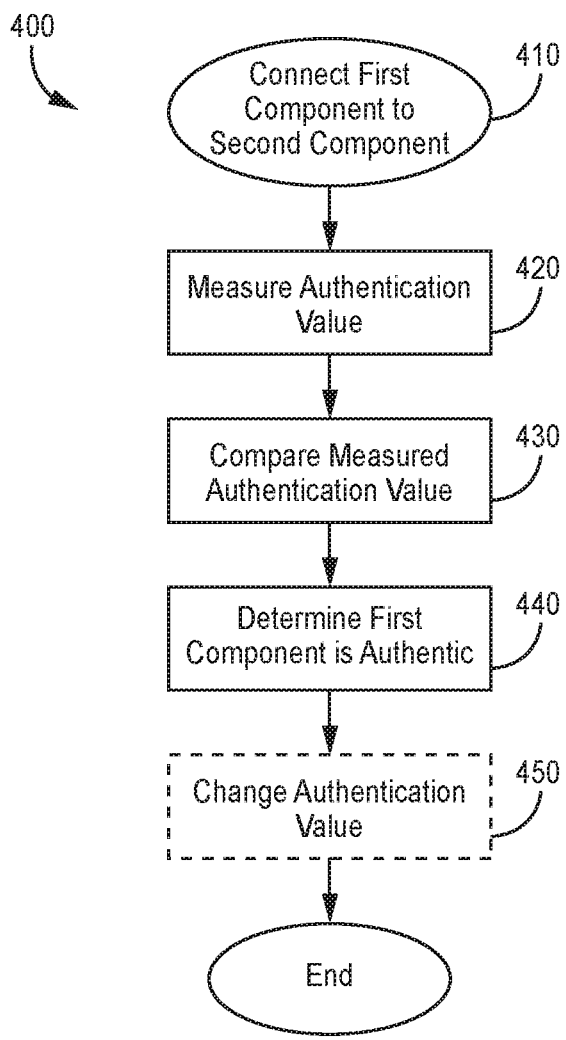
FIG. 4 a flow diagram of an exemplary embodiment of a method for authenticating a connected component.

FIG. 4 illustrates a flow diagram of an exemplary embodiment of a method 400 for authenticating a first component. As one example, this first component could be the control device disclosed herein for use with the injection system. At step 410, the method 400 includes connecting a first component to a second component. The connection can include any two components that are removably connected in any one of a variety of systems. In one particular embodiment, this can include connecting a control device to a control panel of a medical fluid injection system. In certain other embodiments, this can include connecting any other two components of a medical fluid injection system.

At step 420, the method includes measuring an authentication value. This step can include outputting a current from the second component onto a conductive authentication element of the first component and measuring an authentication value associated with the conductive authentication element. For instance, the authentication value may be measured while the current is being output onto the conductive authentication element and/or after the current being output onto the conductive authentication element has ceased. In one embodiment, the conductive authentication element (e.g., a conductive layer, such as a deposited conductive material, printed circuit board) can be the same as, or similar to, the conductive authentication element disclosed herein with respect to the control device. The authentication value may be defined be, and measured at, a sensing trace of the conductive authentication element.

At step 430, the method includes comparing the measured authentication value to a predetermined value. For instance, the predetermined value could be stored at the second component. As examples, the predetermined value could be a range on impedance values of the sensing trace and/or a range of times it takes to fuse the sensing trace.

At step 440, the method includes determining that the first component is authentic when the measured authentication value matches the predetermined value. For example, when the first component is determined to be authentic the second component uses a control signal received from the first component. Whereas, if the first component is determined to not be authentic the second component prevent use of the first component, such as by not using the control signal received from the first component. As such, it can be the case that only a first component determined to be authentic will be recognized by, and operable with, the second component. Determining if the first connected component is authentic, by comparing the measured authentication value to the predetermined value, can include determining if the first connected component is appropriate for use with the second component. As one example, determining if the first connected component is authentic can include determining if the first connected component has been used previously a predetermined number of times. In one instance, by comparing the measured authentication value to the predetermined value, a determination can be made as to whether a connected control device of a medical fluid injection system has been used, for example, once before.

At step 450, the method may include changing the authentication value. In some cases, the method may not include step 450, for instance where it has been determined that the first component is not authentic. In those cases where the step 450 is included, after determining that the first component is authentic, the authentication value associated with the conductive authentication element of the first component can be changed to differ from the predetermined value. By changing the authentication value, the first component can be prevented from being determined as authentic upon a subsequent use since the authentication value at this time will differ from the predetermined value. The authentication value can be changed in a number of ways and in some instance the authentication value can be changed by the second component. As one example, the authentication value can be changed by fusing the conductive authentication element. For instance, where the predetermined value is a range on impedance values of the sensing trace and/or a range of times it takes to fuse the sensing trace, this may change an impedance value and/or time to fuse associated with the sensing trace on the conductive authentication element.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A hand control device comprising:
   a first button that when activated is configured to cause a first control signal to be output from the hand control device to a fluid injection system, wherein the first control signal corresponds to a signal selected from the group consisting of: a start/stop fluid delivery command and a fluid delivery rate command; and
   a hand control device fitting, wherein the hand control device fitting includes a connection device having a connector element and a conductive authentication element, wherein the connector element is configured to connect the hand control device to the fluid injection system and the conductive authentication element is configured to allow the fluid injection system to authenticate the hand control device for use with the fluid injection system.

2. The control device of claim 1, wherein the conductive authentication element includes a first contact trace and a sensing trace that is spaced from the first contact trace, wherein the first contact trace is configured at the connection device so as to contact a first electrical output at the fluid injection system when the connector element is connected to the fluid injection system, and wherein the sensing trace has an associated authentication value usable by the fluid injection system to authenticate the hand control device.

3. The control device of claim 2, wherein the conductive authentication element includes a second contact trace that is spaced from the first contact trace and the sensing trace, wherein the second contact trace is configured at the connection device so as to contact a second electrical output at the fluid injection system when the connector element is connected to the fluid injection system.

4. The control device of claim 3, wherein the sensing trace is located on the conductive authentication element between the first contact trace and the second contact trace.

5. The control device of claim 3, wherein the conductive authentication element includes a first wall that separates the first contact trace from the sensing trace and a second wall that separates the second contact trace from the sensing trace, and wherein the first wall and the second wall are made of an insulating material.

6. The control device of claim 3, wherein an area of the first contact trace is greater than an area of the sensing trace, and wherein an area of the second contact trace is greater than an area of the sensing trace.

7. The control device of claim 2, wherein the authentication value associated with the sensing trace usable by the fluid injection system to authenticate the and control device is an impedance value of the sensing trace.

8. The control device of claim 2, wherein the authentication value associated with the sensing trace usable by the fluid injection system to authenticate the hand control device is a time it takes to fuse the sensing trace.

9. The control device of claim 1, wherein the connector element includes a perimeter ring that is configured to secure the conductive authentication element to the connector element.

10. The control device of claim 9, wherein the connector element includes a central extension configured to connect the hand control device to the fluid injection system, and wherein the perimeter ring is disposed between the central extension and the conductive authentication element.

11. The control device of claim 1, wherein the fluid delivery rate command corresponds to a first fluid type fluid delivery rate command for the fluid injection system.

12. The control device of claim 11, wherein the first button is configured to be pressure-sensitive in its activation such that as varying pressure is applied to the first button the first fluid type fluid delivery rate command output from the hand control device varies according to the varying pressure applied to the first button.

13. The control device of claim 11, further comprising a second button that when activated is configured to cause a second control signal to be output from the hand control device to the fluid injection system, wherein the second control signal corresponds to a second fluid type start/stop fluid delivery command for the controllable component.

14. A system, for authenticating a control device, the system comprising:
   a controllable component storing a predetermined value; and
   the control device in communication with the controllable component, the control device comprising:
      a first button that when activated is configured to output a first control signal to the controllable component, and
      a control device fitting that includes a connection device having a connector element and a conductive authentication element, wherein the connector element is configured to connect the control device to the controllable component, and wherein the conductive authentication element includes a first contact trace and a sensing trace that is spaced from the first contact trace, wherein the first contact trace is in contact with a first electrical output at the controllable component, and wherein the sensing trace defines an authentication value,
   wherein the controllable component is configured to measure the authentication value associated with the conductive authentication element and compare the measured authentication value to the predetermined value and determine that the control device is authentic when the measured authentication value matches the predetermined value.

15. The system of claim 14, wherein the predetermined value is selected from the group consisting of i) a range of impedance values of the sensing trace, and ii) a range of times it takes for the controllable component to fuse the sensing trace.

16. The system of claim 14, wherein, after the controllable component has determined that the control device is authentic, the controllable component is configured to change the authentication value defined by the sensing trace to differ from the predetermined value.

17. The system of claim 16, wherein the controllable component is configured to change the authentication value by fusing the sensing trace when the control device is connected to the controllable component.

18. The system of claim 14, wherein when the controllable component determines that the control device is authentic the controllable component uses the first control signal, and wherein when the measured authentication value does not match the predetermined value the controllable component determines that the control device is not authentic and the controllable component does not use the first control signal.

19. A method for authenticating a first component, the method comprising the steps of:
connecting the first component to a second component, wherein the second component includes a first electrical output;
outputting a current from the second component onto a conductive authentication element of the first component, wherein the conductive authentication element includes a first contact trace and a sensing trace that is spaced from the first contact trace, wherein the first contact trace is in contact with the first electrical output at the second component, and wherein the sensing trace defines the an authentication value;
measuring the authentication value associated with the sensing trace of the conductive authentication element;
comparing the measured authentication value to a predetermined value;
determining that the first component is authentic when the measured authentication value matches the predetermined value, wherein when the first component is determined to be authentic the second component uses a control signal received from the first component; and
after determining that the first component is authentic, changing the authentication value to differ from the predetermined value by fusing the conductive authentication element.

20. The system of claim 14, wherein the control device is a hand control device and the controllable component is a fluid injection system, and wherein the hand control device includes a first button that when activated is configured to cause a first control signal to be output from the hand control device to the fluid injection system, the first control signal corresponding to a signal selected from the group consisting of: a start/stop fluid delivery command and a fluid delivery rate command.

* * * * *